(12) United States Patent
Canali et al.

(10) Patent No.: US 6,541,646 B2
(45) Date of Patent: Apr. 1, 2003

(54) METHOD OF PREPARING COX-2 INHIBITORS

(75) Inventors: Laetitia Canali, Sainte Colombe (FR); Paul Cruciani, Genas (FR); Gilles Oddon, Lyons (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 10/117,832

(22) Filed: Apr. 8, 2002

(65) Prior Publication Data

US 2003/0028036 A1 Feb. 6, 2003

Related U.S. Application Data

(63) Continuation of application No. PCT/FR00/02770, filed on Oct. 5, 2000.

(30) Foreign Application Priority Data

Oct. 8, 1999 (FR) .............................................. 99 12583

(51) Int. Cl.$^7$ .............................................. C07D 407/00
(52) U.S. Cl. ...................................... 549/295; 549/313
(58) Field of Search ................................ 549/295, 313

(56) References Cited

FOREIGN PATENT DOCUMENTS

| WO | WO 97/14691 | 4/1997 |
| WO | WO 97/45420 | 12/1997 |
| WO | WO 98/41516 | 9/1998 |

OTHER PUBLICATIONS

Kitamura et al., "Ipso Substitution of Triarylvinyl Cations by Alkoxide Anions", Journal of the American Chemical Society, vol. 113, No. 19, pp. 7255–7261, 1991, referred to as XP–002145832.

Adam et al., "Epoxidation of Enol Silyl Ethers, Phosphates, Esters, and Lactones by Dimethyldioxirane", Chemische Berichte, vol. 124, pp. 2361–2368, 1991, XP–002145830.

Stevens et al., "Epoxyethers. IV. Mechanism of the Opening of an Epoxyether with an Organic Acid", Journal of the American Chemical Society, vol. 75, pp. 5975–5978, 1953, referred to as XP–002145831.

Murray et al., "Dioxiranes: Synthesis and Reactions of Methyldioxiranes", Journal of Organic Chemistry, vol. 50, No. 16, 1985, XP–002045042.

*Primary Examiner*—Amelia Owens
(74) *Attorney, Agent, or Firm*—Frommer Lawrence & Haug LLP; William S. Frommer; Thomas J. Kowalski

(57) ABSTRACT

The invention relates to a method for producing compounds of general formula (I) wherein $R_1$ is selected from the following groups: (a) $OR_5$ and (b) mono-, di-, or tri-substituted phenyl; and $R_2$ represents a group ($C_1$–$C_6$) alkyl. The method is characterized in that it comprises the following steps: a) reacting a compound of general formula (III) with an acid of general formula $R_1CH_2$ COOH (III) in a water-free medium; b) reacting the resulting compound with a strong base in an aprotic solvent in order to obtain an intermediate cyclic compound which forms a compound of general formula (I) after dehydration; and c) isolating said resulting compound of general formula (I).

21 Claims, No Drawings

METHOD OF PREPARING COX-2 INHIBITORS

This is a continuation of copending international application PCT/FR00/02770 having an international filing date of Oct. 5, 2000.

BACKGROUND OF THE INVENTION

The invention concerns a method of preparing (4-alkylsulphonyl)-phenyl-2-(5H)-furanones, which are compounds inhibiting cyclooxygenase-2 (COX-2); as well as novel intermediate compounds useful for preparing these compounds.

(4-alkylsulphonyl)-phenyl-2-(5H)-furanone compounds useful as COX-2 inhibitors and their pharmacological applications as anti-inflammatories are known and described in the following documents: WO 97/44027, WO 97/28121, WO 98/41516, WO 96/19469, WO 97/16435 and WO 97/14691.

The synthesis of these compound involves a method in several steps involving an intermediary of the 4-alkylsulphonyl-α-bromoisobutyrophenone type.

Thus WO 97/45420 describes a method of preparing (methyl-4-sulphonyl)-phenyl-2-(5H)-furanones from thioanisole involving five steps.

The second step of this method consists of brominating 4-thiomethyl-isobutyrophenone in order to obtain 4-thiomethyl-α-bromoisobutyrophenone.

In the following step the 4-thiomethyl-α-bromoisobutyrophenone is oxidised to 4-methylsulphonyl-α-bromoisobutyrophene, which is a highly allergenic compound, and this compound is then esterified with a carboxylic acid in order to form a 2-methyl-1-(4'-methylsulphonylphenyl)-1-oxo-prop-2-yl ester.

This reaction is also accompanied by a certain number of by-products, including an elimination product, 4-(4'-methylsulphonylphenyl)-2-methyl-propenone.

The aim of the invention is to propose an alternative to the method described in WO 97/45420 and in particular a general method of preparing substituted (4-alkylsulphonylphenyl)2-(5H)-furanone compounds which avoids the problem posed by the α-bromoisobutyrophenone-type intermediary, is easy to implement, avoids the formation of the elimination by-product and provides an acceptable yield of final product.

SUMMARY AND DESCRIPTION OF THE INVENTION

The work carried out by the inventors has now made it possible to propose a method meeting these expectations, and which in particular avoids passing through a toxic bromosulphone derivative and the formation of the aforementioned by-product.

The object of the invention is thus a method of preparing compounds of general formula I:

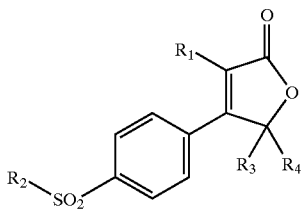

(I)

in which
$R_1$ is chosen amongst the groups
  (a) $OR_5$ where $R_5$ represents a group chosen from amongst
    (1) a $C_1$–$C_6$ branched linear or ring alkyl group;
    (2) a mono-, di- or tri-substituted phenyl or naphthyl group in which the substituents are chosen from amongst:
      hydrogen;
      halogen;
      ($C_1$–$C_3$) alkoxy;
      CN;
      ($C_1$–$C_3$) fluoroalkyl;
      ($C_1$–$C_3$) alkyl;
      COOH;
  and
  (b) mono-, di or tri-substituted phenyl in which the substituents are chosen from amongst:
    hydrogen;
    halogen;
    ($C_1$–$C_3$) alkoxy;
    CN;
    ($C_1$–$C_3$) fluoroalkyl;
    ($C_1$–$C_3$) alkyl;
    COOH;
$R_2$ represents a ($C_1$–$C_6$) alkyl group;
$R_3$ and $R_4$ represents independently of one another a hydrogen atom or a $CHR_6R_7$ group
in which $R_6$ and $R_7$ are independently of each other chosen from amongst:
  hydrogen;
  ($C_1$–$C_{10}$) alkyl;
  ($C_1$–$C_{10}$) alkoxy;
  OH;
  CN;
  $CH_2CN$;
  $OCOR_8$;
  ($C_1$–$C_6$) fluoroalkyl;
  halogen;
  CON ($R_8$)$_2$;
  mono-, di or tri-substituted phenyl;
  mono-, di or tri-substituted heteroaryl;
the substituents being chosen from amongst:
  hydrogen;
  halogen;
  ($C_1$–$C_6$) alkyl;
  ($C_1$–$C_{10}$) alkoxy;
  CN;
  $CF_3$;
  $N_3$;
  C ($R_9$) ($R_{10}$)—OH;
  C ($R_9$) ($R_{10}$) —O—($C_1$–$C_4$) alkyl;

($C_1$–$C_6$) fluoroalkyl;

$R_8$ is chosen from amongst;

- hydrogen;
- ($C_1$–$C_6$) alkyl;
- mono-, di- or tri-substituted phenyl, the substituents being chosen from amongst hydrogen, halogen, ($C_1$–$C_6$) alkyl, ($C_1$–$C_6$) alkoxy, ($C_1$–$C_6$) alkylthio, CN or $CF_3$; and
- mono-, di or tri-substituted benzyl, the substituents being chosen from amongst hydrogen, halogen, ($C_1$–$C_6$) alkyl, ($C_1$–$C_6$) alkoxy, ($C_1$–$C_6$) alkylthio, CN or $CF_3$;

or two $R_8$ groups from together with the nitrogen atom to which they are attached a ring with 5 to 7 atoms, and possibly comprising a heteroatom chosen from amongst O, S or $NR_9$;

$R_9$ and $R_{10}$ are independently of one another chosen from amongst:

- hydrogen; and
- ($C_1$–$C_{10}$) alkyl; or form, together with the atom to which they are attached, a ring with 3 to 7 carbon atoms and where applicable a nitrogen atom;

wherein it comprises the following steps:

a) reaction of a compound of general formula II:

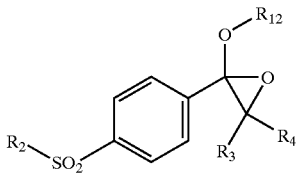

(II)

in which $R_2$, $R_3$ and $R_4$ are as defined above and $R_{12}$ represents a $C_1$–$C_6$ alkyl group, with an acid of general formula III:

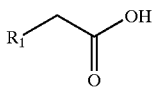

(III)

in which $R_1$ is as defined previously, in an anhydrous medium, in order to form a compound of formula IV:

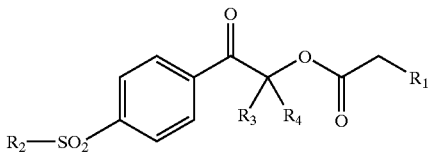

(IV)

$R_1$, $R_2$, $R_3$ and $R_4$ being as defined above;

b) reaction of the compound of formula IV with a strong base in an aprotic solvent in order to obtain an intermediate ring compound of formula V:

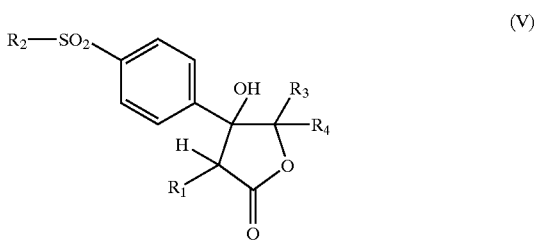

(V)

which, after elimination of a water molecule, forms a compound of general formula I; and c) isolation of the compound of general formula I thus obtained.

The reaction of step a) takes place in an anhydrous solvent, preferably an ether, for example diethylether, or methyltertbutylether. The reaction temperature is advantageously between –20 and 40° C. At the end of step a), a compound of general formula IV is obtained as well as secondary products in minor quantities. However, the aforementioned elimination product does not form.

For the reaction of step b), the strong base is advantageously chosen from amongst 1,8-diazabicyclo[5.4.0]undec-7-ene (DBU), 1,4-diazabicyclo[2.2.2]octane (DABCO) and 1,5-diazabicyclo[4.3.0]non-5-ene (DBN).

The elimination of a water molecule is achieved in a manner known per se, advantageously by thermal dehydration in the presence of a dehydration agent.

The dehydration agent can be chosen in particular from amongst trifuloroacetic acid esters, for example isopropyl trifluoroacetate, trichloracetic acid esters and alkyl or arylsulphonic acid esters.

The reaction preferably takes place in an aprotic solvent such as acetonitrile, N,N-dimethylformamide, N-methylsulphoxide, proprionitrile or nitromethane.

The dehydration is achieved by heating to reflux.

The molar ratio of the ester of formula IV to the strong base is generally between 1:1 and 1:2, a ratio of 1:1.5 being preferred.

The molar ratio of the ring ester of formula V to the dehydration agent is generally 1:1 to 1:2, a ratio of 1:1.2 being preferred.

The reaction is carried out at a temperature preferably between 0° C. and the reflux temperature of the solvent.

Particularly advantageous reaction conditions are achieved by the use of a mixture of 1.2 equivalents of isopropyl trifluoroacetate and 1.5 equivalents of DBU in acetonitrile at reflux. Under these conditions, the reaction is terminated after 24 hours and the product crystallises by the addition of water after partial elimination of the acetonitrile. For more information, reference should be made to the description of the patent application WO 97/45420.

Step c) is carried out in a manner known per se, in particular by elimination of the solvent, precipitation of the product, recrystallisation, etc.

The epoxy compound of general formula II can be obtained by the reaction of a compound of general formula VI:

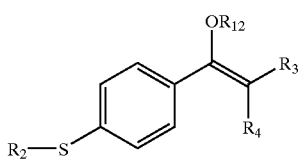

(VI)

in which $R_2$, $R_3$, $R_4$ and $R_{12}$ are as defined above, with an oxidising agent.

Oxidising agents can in particular include organic peracids, such as meta-chloroperbenzoic acid and peracetic acid or dioxiranes such as dimethyldioxirane, generated in situ or not. The reaction temperature is advantageously between −40° C. and 30° C.

The oxidising agent is used in excess with respect to the compound of general formula II (3 to 40 equivalents), so as to oxidise on the one hand the olefin function into epoxide and on the other hand the sulphide function into sulphone.

The compound of general formula VI can be obtained by reaction of a compound of general formula VII:

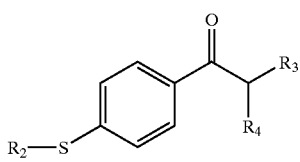

(VII)

in which $R_2$, $R_3$ and $R_4$ are as defined above, with an alcohol of general formula VIII:

HO $R_{12}$ (VIII)

$R_{12}$ being as defined above, in the presence of a catalytic quantity of acid and a dehydrating agent.

Advantageously, the acid is chosen from amongst the sulphonic acids, for example p-toluene sulphonic acid, or the mineral acids, for example hydrochloric acid. By way of dehydrating agent, $C_1$–$C_6$ alkyl orthoformiates are preferred.

The reaction is carried out in an excess of alcohol of general formula VIII, this serving as a reactive solvent.

In the compound of general formula VIII, $R_{12}$ is advantageously a methyl group, the alcohol being methanol.

Another object of the invention is a method of preparing a compound of general formula I as defined above, wherein it comprises the following steps:

(1) reaction of a compound of general formula IX:

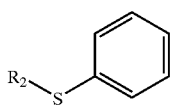

(IX)

in which $R_2$ is as defined above, in a solvent which is inert in the presence of a Lewis acid with a compound of general formula X:

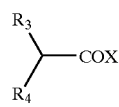

(X)

in which X is a starting group, preferably a chlorine atom, in order to form a compound of general formula VII:

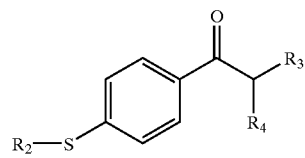

(VII)

in which $R_2$, $R_3$ and $R_4$ are as defined previously, (2) reaction of a compound of general formula VII with an alcohol of general formula VIII:

$R_{12}$–OH (VIII)

in which $R_{12}$ represents a $(C_1$–$C_6)$ alkyl group in order to form a compound of general formula VI:

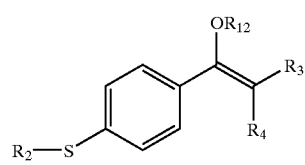

(VI)

in which $R_2$, $R_3$, $R_4$ and $R_{12}$ are as defined above, (3) reaction of the compound of general formula VI with an oxidising agent in order to obtain a compound of general formula II:

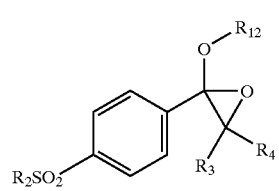

(II)

in which $R_2$, $R_3$, $R_4$ and $R_{12}$ are as defined previously;

(4) reaction of the compound of general formula II as defined at step (3) with an acid of general formula III:

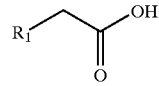

(III)

in which $R_1$ is as defined previously, in an anhydrous medium, in order to form a compound of formula IV:

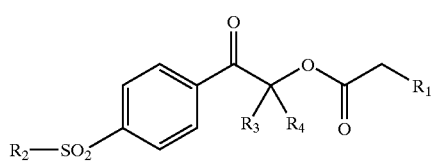

$R_1$, $R_2$, $R_3$ and $R_4$ being as defined above;
(5) reaction of the compound of formula IV with a strong base in an aprotic solvent in order to obtain an intermediate ring compound of formula V:

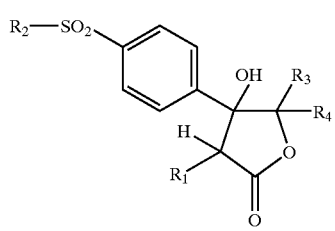

which, after elimination of a water molecule, forms a compound of general formula I; and
(6) isolation of the compound of general formula I thus obtained.

For the reaction of step (1), the Lewis acid is advantageously chosen from amongst $AlCl_3$, $FeCl_3$, $TiCl_4$ and $SnCl_4$ without however being limited to these. The non-reactive solvents comprise halogenated and polyhalogenated hydrocarbons such as the mono- or dihalo($C_1$–$C_4$)alkyls, for example dichloromethane; the aromatic solvents such as nitrobenzene or halogenated aromatic compounds, as well as branched linear or ring $C_6$–$C_{10}$ hydrocarbons comprising notably hexane, cyclohexane, methylcyclohexane or $CS_2$. For this step, cyclohexane or dichlorobenzene can in particular be chosen. The molar ratio of the compound of general formula IX to the compound of general formula X is generally between 1:1.5 and 1.5:1, a ratio of 1:1 to 1:1.5 being preferred. The reaction is generally carried out with an excess of the compound of general formula X. Generally the molar ratio of the compound of general formula IX to the Lewis acid is between 1:1.5 and 1.5:1.

Preferably, the molar ratio of the compound of general formula IX to the Lewis acid is between 1:1 and 1:1.5. The reaction can advantageously be carried out in a temperature range of between 0 and 25° C., preferably 5 and 15° C. The reagents are set to react until the reaction is completed, which occurs after an interval of time ranging from 8 to 4 hours, generally 1 to 2 hours. The reaction is preferably carried out in a nitrogen atmosphere. Steps (2) to (6) are carried out under conditions as described previously.

The compounds of general formula IX and X are commercially available compounds or ones which can easily be prepared by a person skilled in the art using well known routine methods.

In a first embodiment of the method of the invention, $R_1$ is an RO group, R being as defined previously for $R_5$.

The compound of general formula I then becomes a compound of general formula Ia:

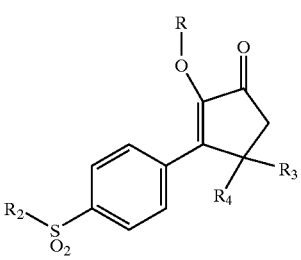

The method according to the invention in this case comprises the following steps:
a) reaction of a compound of general formula II

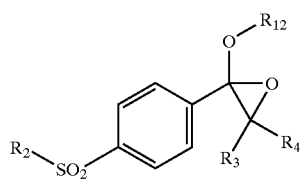

in which $R_2$, $R_3$ and $R_4$ are as defined previously and $R_{12}$ represents a $C_1$–$C_6$ alkyl group,
with an acid of general formula IIIa

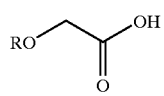

in which R is as defined above, in an anhydrous medium, in order to form a compound of general formula IVa:

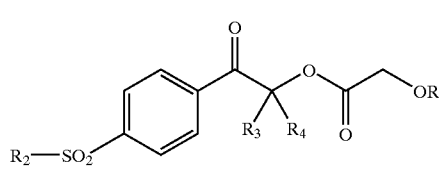

in which R, $R_2$, $R_3$ and $R_4$ are as defined previously;
b) reaction of the compound of formula IVa with a strong base in an aprotic solvent in order to obtain an intermediate ring compound of formula Va:

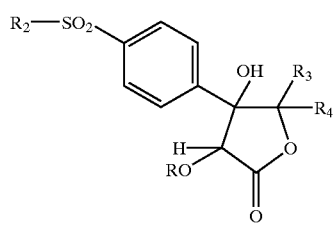

which, after elimination of a water molecule, forms a compound of general formula Ia; and
c) isolation of the compound of general formula Ia thus obtained.

Preference is particularly given to the compounds of general formula Ia in which R represents the cyclopropylmethyl group, and $R_2$, $R_3$ and $R_4$ represent the methyl group.

In a second embodiment of the invention, the group $R_1$ is a substituted phenyl ring.

The compound of general formula I then becomes a compound of general formula Ib:

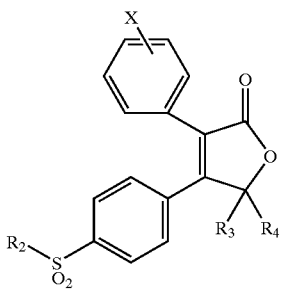

(Ib)

in which $R_2$ is as defined previously and X is chosen from amongst:

hydrogen;
halogen;
($C_1$–$C_3$) alkoxy;
CN;
($C_1$–$C_3$) fluoroalkyl;
($C_1$–$C_3$) alkyl;
—COOH.

The method of the invention then comprises the following steps:

a) reaction of a compound of general formula II

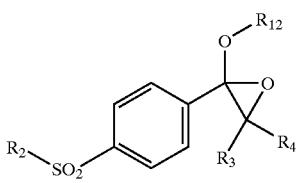

(II)

in which $R_2$, $R_3$ and $R_4$ are as defined previously and $R_{12}$ represents a $C_1$–$C_6$ alkyl group,
with an acid of general formula III b)

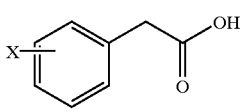

(IIIb)

in which X is as defined previously, in an anhydrous medium, in order to form a compound of general formula IV b)

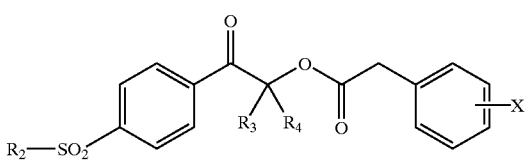

(IVb)

$R_2$, $R_3$ and $R_4$ being as defined above;

b) reaction of the compound of formula IVb with a strong base in an aprotic solvent in order to obtain an intermediate ring compound of formula Vb:

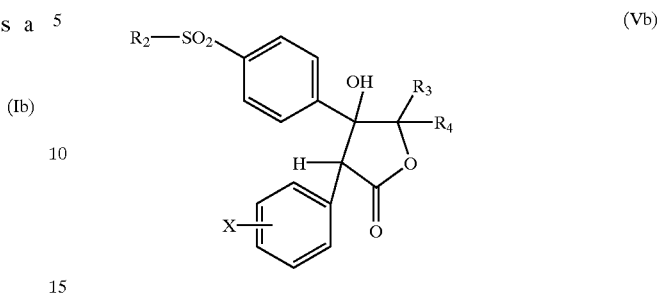

(Vb)

which after elimination of a water molecule, forms a compound of general formula Ib;

c) isolation of the compound of general formula Ib thus obtained.

The intermediate compound of general formula VI is novel and constitutes another object of the invention.

In particular the compounds of general formula IV in which $R_2$, $R_3$ and $R_4$ represent the methyl group and $R_{12}$ is as defined above are preferred.

A particularly preferred compound of this type in the one in which $R_{12}$ represents methyl.

The method of the invention is illustrated by means of the following example:

EXAMPLE

Preparation of 3-(cyclopropylmethoxy)-[4-(4-methylsulphonyl)phenyl)]-5,5-dimethyl-5-H-furan-2-one.

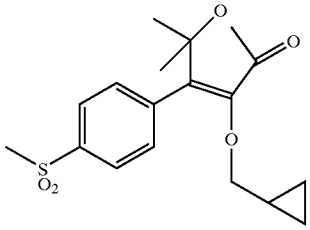

Preparation of 1-methoxy-2-methyl-1-(4'-methylthiophenyl)prop-1-ene:

p-toluene sulphonic acid (1.2 g, 6.3 mmol, 0.12 equiv) is added to a solution of 2-methyl-1-(4'-methylthiophenyl) propan-1-one or (4-thiomethyl-isobutyrophenone (compound 2; 10.11 g, 52 mmol, 1 equiv) obtained as described in Example 1 from WO 97/45420) by reaction of thioanisole in the presence of a Lewis acid with isobutyryl chloride in a mixture of methanol (40 ml)/methyl orthoformate (40 ml). This solution is heated for 1.5 hours to reflux and then the methanol is distilled. The reactional mass is then heated for 41 hours at 115° C. After return to room temperature, the reactional mixture is diluted with dichloromethane (50 ml), washed with a saturated aqueous solution of potassium carbonate (50 ml) and then with brine (50 ml) and dried on sodium sulphate. Evaporation of the solvents supplies a mixture of the expected 1-methoxy-2-methyl-1-(4'-methylthiophenyl)prop-1-ene and 1,1-dimethoxy-2-methyl-1-(4'-methylthiophenyl)propane in a molar ratio of 83/17 (10.0 g).

RMN—¹H (200 MHz, CDCl₃) ppm:

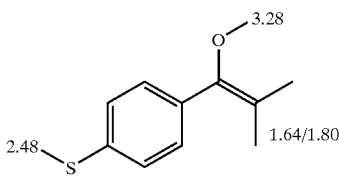

(3)

GC/IR/MS:
m/z: 208
IR (cm⁻¹): aromatic C—H 3073; O—CH₃ 2872, 2840; C=C 1668, C—O—C 1143.

2) Preparation of 3,3-dimethyl-2-methoxy-2-(4'-methylsulphonylphenyl) oxirane:

Oxone® (dimethyldioxirane) (78.9 g, 128.3 mmol, 6.3 equiv) is added to a suspension of sodium hydrogenocarbonate (38.14 g, 454.0 mmol) in a mixture of acetone (126 ml)/water (167 ml) at 0° C. in 5 portions at intervals of 3 mintues. A solution of raw 1-methoxy-2-methyl-1-(4'-methylthiophenyl)prop-1-ene (4.24 g, 20.3 mmol) in dichloromethane (10 ml) is added to the reaction mixture. The ice bath is removed and the mixture is stirred for 3.5 hours at room temperature. The reaction medium is then filtered and the filtrate is extracted with dichloromethane (5×5 ml). The assembled organic phases are dried on sodium sulphate and concentrated in order to supply expected 3,3-dimethyl-2-methoxy-2-(4'-methylsulphonylphenyl)oxirane expected (compound 4; 3.80 g).

RMN—¹H (200 MHz, CDCl₃) ppm:

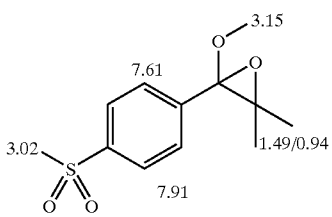

(4)

GC/IR/MS:
m/z: 241 (M-15); 183
IR (cm⁻¹): O—CH₃ 2845; SO₂ 1348, 1164

3) Preparation of [2-methyl-1-(4'-methylsulphonylphenyl)-1-oxo-prop-2-yl] 2-(cyclopropylmethyoxy) acetate:

A solution of raw 3,3-dimethyl-2-methoxy-2-(4'-methylsulphonylphenyl)oxirane (3.6 g, 14.1 mmol) and 2-(cyclopropylmethoxy)acetic acid (2.17 g, 16.7 mmol, 1.2 equiv) in anhydrous tert-butylmethylether (10 ml) is stirred at room temperature for 2 days. The reaction mixture is then concentrated in order to supply a yellow solid (5.24 g) containing 65% p/p of [2-methyl-1-(4'-methylsulphonylphenyl)-1-oxo-prop-2-yl] 2-(cyclopropylmethyoxy)acetate. The concatenated yield from the 2-methyl-1-(4'-methylthiophenyl)propan-1-one is 46% pure/pure.

GC/IR/MS:
M/z: 238; 183
IR (cm⁻¹): C=O 1752, 1711, SO₂ 1349, 1166; C—O—C 1124

4) Preparation of 3-(cyclopropylmethoxy)-5,5-dimethyl-4-(4'-methylsulphonylphenyl)-5H-furan-2-one (title compound)

A solution of isopropyl trifluoroacetate (1.58 g, 10.1 mmol, 1.2 equiv) and 1,8-diazabicyclo-[5.4.0]-undec-7-ene (2.6 g, 13.5 mmol, 1.6 equiv) in anhydrous acetonitrile (20 ml) is stirred for 15 minutes at room temperature. [2-methyl-1-(4'-methylsulphonylphenyl)-1-oxo-prop-2-yl] 2-(cyclopropylmethoxy)acetate (3.00 g, 8.4 mol) is then added and the reaction mixture is heated to reflux for 18 hours. After returning the temperature to 40° C. the acetonitrile is partially evaporated and then water (20 ml) is added to the reaction medium. After returning to room temperature and a few hours of crystallisation, the mixture is filtered in order to recover the expected 3-(cyclopropylmethoxy)-5,5-dimethyl-4-(4'-methylsulphonyl)-5H-furan-2-one. The yield of isolated product is 85%.

RMN-¹H (200 MHz, CD₃COCD₃) ppm:

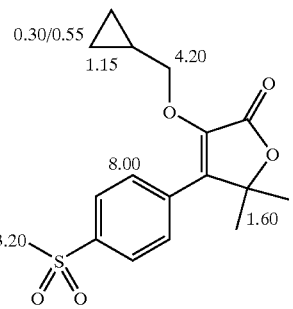

We claim:
1. A method of preparing compounds of general formula I:

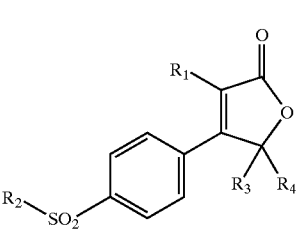

(I)

in which $R_1$ is chosen from the group consisting of
(a) $OR_5$ where $R_5$ represents a group chosen from amongst the group consisting of
(1) a $C_1$–$C_6$ branched linear and ring alkyl group;
(2) amongst the group consisting of a mono-, di- and tri- substituted phenyl and naphthyl group in which the substituents are chosen from amongst:
hydrogen;
halogen;
$(C_1$–$C_3)$alkoxy;
CN;
$(C_1$–$C_3)$fluoroalkyl;
$(C_1$–$C_3)$alkyl;
COOH; and
(b) amongst a group consisting of mono-, di and tri-substituted phenyl in which the substituents are chosen from amongst:
hydrogen;
halogen;
$(C_1$–$C_3)$alkoxy;
CN;
$(C_1$–$C_3)$fluoroalkyl;
$(C_1$–$C_3)$alkyl;
COOH;

$R_2$ represents a $(C_1-C_6)$ alkyl group;

$R_3$ and $R_4$ represent independently of one another a constituent chosen from the group consisting of a hydrogen atom and a $CHR_6R_7$ group in which $R_6$ and $R_7$ are independently of each other chosen from amongst:
hydrogen;
$(C_1-C_{10})$alkyl;
$(C_1-C_{10})$alkoxy;
OH;
CN;
$CH_2CN$;
$OCOR_8$;
$(C_1-C_6)$fluoroalkyl;
halogen;
$CON(R_8)_2$;
a phenyl chosen from the group consisting of mono-, di- and tri-substituted phenyl;
a heteroaryl chosen from the group consisting of mono-, di and tri-substituted heteroaryl;
the substituents being chosen from amongst the group consisting of:
hydrogen;
halogen;
$(C_1-C_6)$alkyl;
$(C_1-C_{10})$alkoxy;
CN;
$CF_3$;
$N_3$;
$C(R_9)(R_{10})$—OH;
$C(R_9)(R_{10})$—O—$(C_1-C_4)$alkyl;
$(C_1-C_6)$fluoroalkyl;

wherein $R_8$ is chosen from amongst the group consisting of:
hydrogen;
$(C_1-C_6)$alkyl;
a phenyl chosen from the group consisting of mono-, di and tri-substituted phenyl, the substituents being chosen from amongst the group consisting of hydrogen, halogen, $(C_1-C_6)$alkyl, $(C_1-C_6)$alkoxy, $(C_1-C_6)$alkylthio, CN and $CF_3$; and
a benzyl chosen from the group consisting of mono-, di and tri-substituted benzyl, the substituents being chosen from amongst the group consisting of hydrogen, halogen, $(C_1-C_6)$alkyl, $(C_1-C_6)$alkoxy, $(C_1-C_6)$alkylthio, CN and $CF_3$; including the group (s) consisting of:

two $R_8$ groups form together with the nitrogen atom to which they are attached a ring with 5 to 7 atoms, and possibly comprising a heteroatom chosen from amongst the group consisting of O, S and $NR_9$;

wherein $R_9$ and $R_{10}$ are independently of one another chosen from amongst the group consisting of:
(i) hydrogen and
$(C_1-C_{10})$alkyl; and
(ii) where $R_9$ and $R_{10}$ form, together with the atom to which they are attached, a ring with 3 to 7 carbon atoms and where applicable a nitrogen atom;

wherein the method comprises the following steps:
a) reaction of a compound of general formula II:

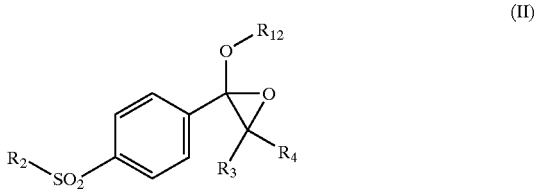

in which $R_2$, $R_3$ and $R_4$ are as defined above and $R_{12}$ represents a $C_1-C_6$ alkyl group,
with an acid of general formula III:

in which $R_1$ is as defined previously, in an anhydrous medium, in order to form a compound of formula IV:

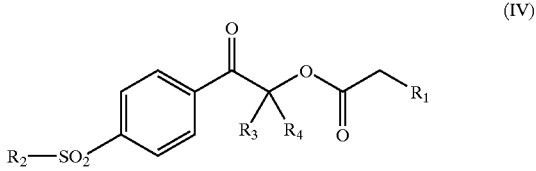

$R_1$, $R_2$, $R_3$ and $R_4$ being as defined above;
b) reaction of the compound of formula IV with a strong base in an aprotic solvent in order to obtain an intermediate ring compound of formula V:

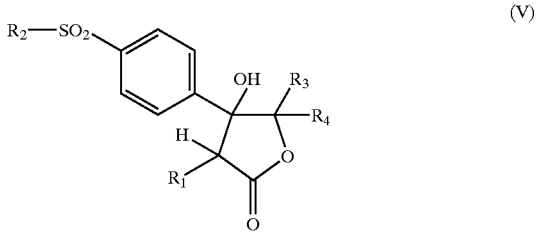

which, after elimination of a water molecule, forms a compound of general formula I; and
c) isolation of the compound of general formula I thus obtained.

2. A method according to claim 1, wherein the compound of general formula II is prepared by reacting a compound of general formula VI:

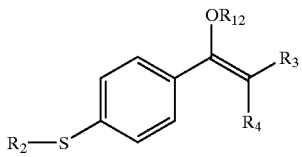

in which $R_2$, $R_3$, $R_4$ and $R_{12}$ are as defined in claim 1, with an oxidising agent.

3. A method according to claim 2, wherein the compound of general formula VI as defined in claim 2 is prepared by reacting a compound of general formula VII:

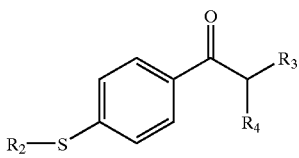

(VII)

in which $R_2$, $R_3$ and $R_4$ are as defined in claim 1, with an alcohol of general formula VIII:

HO R$_{12}$ (VIII)

$R_{12}$ being as defined claim 1, in the presence of a catalytic quantity of acid and a dehydrating agent.

4. A method according to claim 3, wherein $R_{12}$ is methyl and the compound of general formula VIII is methanol.

5. A method of preparing a compound of general formula I as defined in claim 1, wherein the method comprises the following steps:

(1) reaction of a compound of general formula IX:

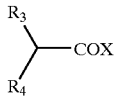

(IX)

in which $R_2$ is as defined in claim 1, in a solvent which is inert in the presence of a Lewis acid with a compound of general formula X:

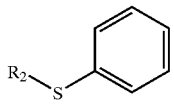

(X)

in which X is a starting group, preferably a chlorine atom, in order to form a compound of general formula VII:

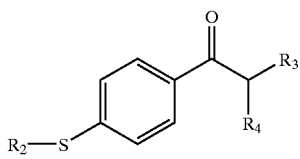

(VII)

in which $R_2$, $R_3$ and $R_4$ are as defined in claim 1, (2) reaction of the compound of general formula VII with an alcohol of general formula VIII:

$R_{12}$-OH (VIII)

in which $R_{12}$ represents a $(C_1$–$C_6)$alkyl group in order to form a compound of general formula VI:

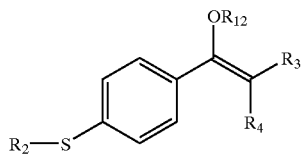

(VI)

in which $R_2$, $R_3$, $R_4$ and $R_{12}$ are as defined in claim 1, (3) reaction of the compound of general formula VI with an oxidising agent in order to obtain a compound of general formula II:

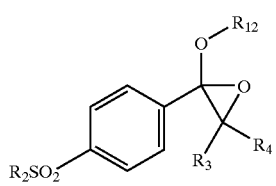

(II)

in which $R_2$, $R_3$, $R_4$ and $R_{12}$ are as defined in claim 1;

(4) reaction of the compound of general formula II as defined as step (3) with an acid of general formula III:

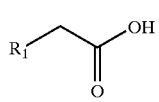

(III)

in which $R_1$ is as defined in claim 1, in an anhydrous medium, in order to form a compound of formula IV:

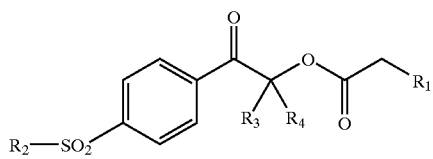

(IV)

$R_1$, $R_2$, $R_3$ and $R_4$ being as defined above;

(5) reaction of the compound of formula IV with a strong base in an aprotic solvent in order to obtain an intermediate ring compound of formula V:

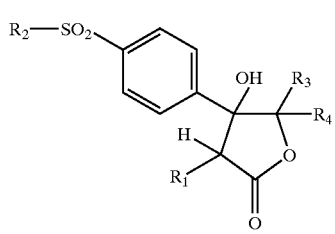

(V)

which, after elimination of a water molecule, forms a compound of general formula I; and (6) isolation of the compound of general formula I thus obtained.

6. A method according to claim 1 for preparing a compound of general formula Ia:

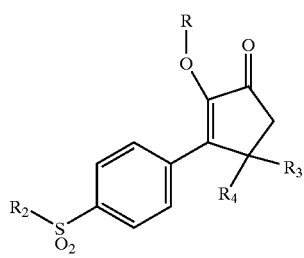
(Ia)

in which R represents a group $R_5$ as defined in claim 1 and $R_2$, $R_3$ and $R_4$ are as defined in claim 1, wherein the method comprises the following steps:
  a) reaction of a compound of general formula II

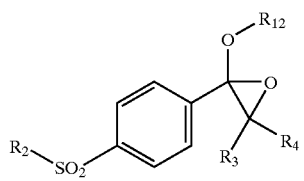
(II)

in which $R_2$, $R_3$ and $R_4$ are as defined in claim 1 and $R_{12}$ represents a $C_1$–$C_6$ alkyl group, with an acid of general formula IIIa:

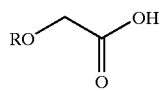
(IIIa)

in which R is as defined above, in an anhydrous medium, in order to form a compound of general formula IVa:

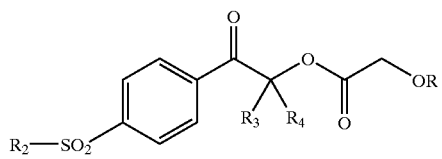
(IVa)

in which R, $R_2$, $R_3$ and $R_4$ are as defined in claim 1;
  b) reaction of the compound of formula IVa with a strong base in an aprotic solvent in order to obtain an intermediate ring compound of formula Va:

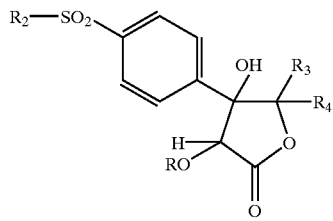
(Va)

which, after elimination of a water molecule, forms a compound of general formula Ia;
  c) isolation of the compound of general formula Ia thus obtained.

7. A method according to claim 1 for preparing a compound of general formula Ib:

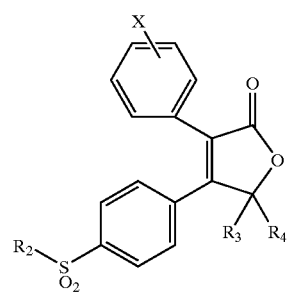
(Ib)

in which $R_2$ is as defined in claim 1 and X is chosen from amongst:

hydrogen;
halogen;
$(C_1$–$C_3)$alkoxy;
CN;
$(C_1$–$C_3)$fluoroalkyl;
$(C_1$–$C_3)$alkyl;
—COOH;

wherein the method comprises the following steps:
  a) reaction of a compound of general formula II

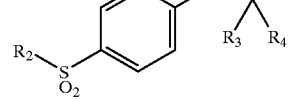
(II)

in which $R_2$, $R_3$ and $R_4$ are as defined in claim 1 and $R_{12}$ represents a $C_1$–$C_6$ alkyl group, with an acid of general formula IIIb)

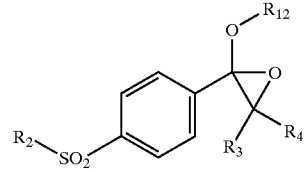
(IIIb)

in which X is as defined in claim 1, in an anhydrous medium, in order to form a compound of general formula IVb)

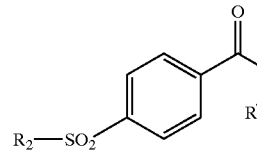
(IVb)

$R_2$, $R_3$ and $R_4$ being as defined in claim 1;
  b) reaction of the compound of formula IVb with a strong base in an aprotic solvent in order to obtain intermediate ring compound of formula Vb:

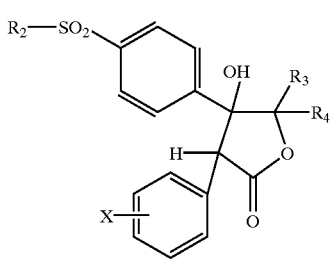

which, after elimination of a water molecule, forms a compound of general formula Ib;

c) isolation of the compound of general formula Ib thus obtained.

8. A method of preparing the compound of formula (1):

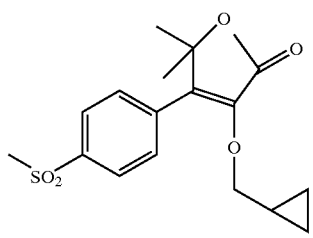

including the following steps:

reaction of thioanisole in the presence of a Lewis acid with isobutyryl chloride in order to obtain the compound of formula (2)

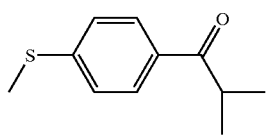

reaction of the compound of formula (2) with methanol in the presence of para-toluene sulphonic acid and methyl orthoformiate in order to form the compound of formula (3):

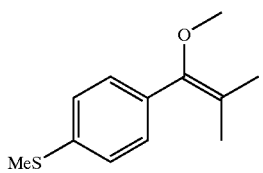

reaction of compound (3) with dimethyldioxirane in order to form the compound of formula (4):

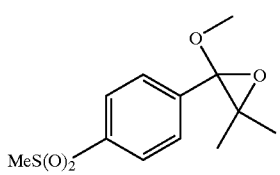

reaction of compound (4) with cyclopropylmethyloxy acetic acid in an anhydrous solvent in order to obtain compound (5):

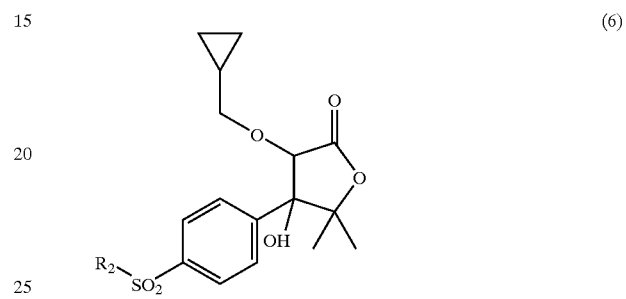

reaction of compound (5) in an aprotic solvent with a strong base in order to obtain an intermediate ring compound (6):

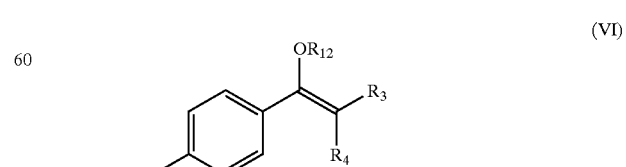

which, after dehydration in the presence of a dehydrating agent, forms compound (1).

9. A method according to claim 2, wherein the oxidising agent is chosen from amongst organic peracids, and dioxiranes.

10. A method according to claim 5, wherein the oxidising agent is chosen from amongst organic peracids, and dioxiranes.

11. A method according to claim 2, wherein the temperature of the oxidation reaction is between −40° and 30° C.

12. A method according to claim 5, wherein the temperature of the oxidation reaction is between −40° and 30° C.

13. A method according to claim 2, wherein the oxidising agent is used in excess with respect to the compound of general formula II.

14. A method according to claim 5, wherein the oxidising agent is used in excess with respect to the compound of general formula II.

15. A method according to claim 3, wherein the acid is chosen from amongst the group consisting of sulphonic acids and mineral acids.

16. A method according to claim 3, wherein, by way of dehydrating agent, $C_1$–$C_6$ alkyl orthoformiate is used.

17. A method according to claim 3, wherein the reaction is carried out in an excess of alcohol of general formula VIII, serving as a reactive solvent.

18. A method according to claim 5, wherein the reaction is carried out in an excess of alcohol of general formula VIII, serving as a reactive solvent.

19. Compound of general formula VI:

in which $R_2$ represents a $(C_1-C_6)$alkyl group;

$R_3$ and $R_4$ represent independently of one another, a constituent selected from the group consisting of a hydrogen atom and a $CHR_6R_7$ group in which $R_6$ and $R_7$ are independently of each other chosen from amongst the group consisting of:
hydrogen;
$(C_1-C_{10})$alkyl;
$(C_1-C_{10})$alkoxy;
OH;
CN;
$CH_2CN$;
$OCOR_8$;
$(C_1-C_6)$fluoroalkyl;
halogen;
$CON(R_8)_2$;
a phenyl selected from the group consisting of mono-, di and tri-substituted phenyl;
a heteroaryl selected from the group consisting of mono-, ti- and ti-substituted heteroaryl;
the substituents being chosen from amongst:
hydrogen;
halogen;
$(C_1-C_6)$alkyl;
$(C_1-C_{10})$alkoxy;
CN;
$CF_3$;
$N_3$;
$C(R_9)(R_{10})$-OH;
$C(R_9)(R_{10})$-O-$(C_1-C_4)$alkyl;
$(C_1-C_6)$fluoroalkyl;
$R_8$ is chosen from amongst the group consisting of:
hydrogen;
$(C_1-C_6)$alkyl;
a phenyl selected from the group consisting of mono-, di- and tri-substituted phenyl, the substituents being chosen from amongst the group consisting of hydrogen, halogen, $(C_1-C_6)$alkyl, $(C_1-C_6)$alkoxy, $(C_1-C_6)$alkylthio, CN and $CF_3$; and
a benzyl selected from the group consisting of mono-, di- and tri-substituted benzyl, the substituents being chosen from amongst the group consisting of hydrogen, halogen, $(C_1-C_6)$alkyl, $(C_1-C_6)$alkoxy, $(C_1-C_6)$alkylthio, CN and $CF_3$;
including the group(s) consisting of:
two $R_8$ groups forming together with the nitrogen atom to which they are attached a ring with 5 to 7 atoms, and possibly comprising a heteroatom chosen from amongst the group consisting of O, S and $NR_9$;
wherein $R_9$ and $R_{10}$ are independently of one another chosen from amongst the group consisting of:
(i) hydrogen; and
$(C_1-C_{10})$alkyl; and
(ii) where $R_9$ and $R_{10}$ form, together with the atom to which they are attached, a ring with 3 to 7 carbon atoms and where applicable a nitrogen atom;
and $R_{12}$ represents a $C_1-C_6$ alkyl group.

20. A compound of formula

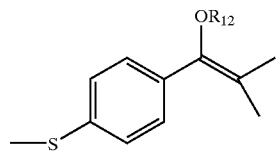

in which $R_{12}$ is as defined in claim 15, in particular methyl.

21. Method of preparing compounds of general formula I:

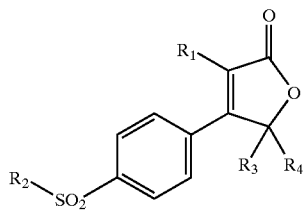

(I)

in which
$R_1$ is chosen from amongst the groups
(a) $OR_5$ where $R_5$ represents a group chosen from amongst
(1) a $C_1-C_6$ branched linear or ring alkyl group;
(2) a mono-, di- or tri-substituted phenyl or naphthyl group in which the substituents are chosen from amongst:
hydrogen;
halogen;
$(C_1-C_3)$alkoxy;
CN;
$(C_1-C_3)$fluoroalkyl;
$(C_1-C_3)$alkyl;
COOH; and
(b) mono-, di- or tri-substituted phenyl in which the substituents are chosen from amongst:
hydrogen;
halogen;
$(C_1-C_3)$alkoxy;
CN;
$(C_1-C_3)$fluoroalkyl;
$(C_1-C_3)$alkyl;
COOH;
$R_2$ represents a $(C_1-C_6)$ alkyl group;
$R_3$ and $R_4$ represent independently of one another a hydrogen atom or a $CHR_6R_7$ group
in which $R_6$ and $R_7$ are independently of each other chosen from amongst:
hydrogen;
$(C_1-C_{10})$alkyl;
$(C_1-C_{10})$alkoxy;
OH;
CN;
$CH_2CN$;
$OCOR_8$;
$(C_1-C_6)$fluoroalkyl;
halogen;
$CON(R_8)_2$;
mono-, di- or tri-substituted phenyl;
mono-, di- or tri-substituted heteroaryl;
the substituents being chosen from amongst:
hydrogen;
halogen;

(C$_1$–C$_6$)alkyl;
(C$_1$–C$_{10}$)alkoxy;
CN;
CF$_3$;
N$_3$;
C(R$_9$)(R$_{10}$)-OH;
C(R$_9$)(R$_{10}$)-O-(C$_1$–C$_4$)alkyl;
(C$_1$–C$_6$)fluoroalkyl;

R$_8$ is chosen from amongst:
  hydrogen;
  (C$_1$–C$_6$)alkyl;
  mono-, di- or tri-substituted phenyl, the substituents being chosen from amongst hydrogen, halogen, (C$_1$–C$_6$)alkyl, (C$_1$–C$_6$)alkoxy, (C$_1$–C$_6$)alkylthio, CN or CF$_3$; and
  mono-, di- or tri-substituted benzyl, the substituents being chosen from amongst hydrogen, halogen, (C$_1$–C$_6$)alkyl, (C$_1$–C$_6$)alkoxy, (C$_1$–C$_6$)alkylthio, CN or CF$_3$;
or two R$_8$ groups form together with the nitrogen atom to which they are attached a ring with 5 to 7 atoms, and possibly comprising a heteroatom chosen from amongst O, S or NR$_9$;

R$_9$ and R$_{10}$ are independently of one another chosen from amongst:
  hydrogen; and
  (C$_1$–C$_{10}$)alkyl; or
form, together with the atom to which they are attached, a ring with 3 to 7 carbon atoms and where applicable a nitrogen atom;

characterised in that it comprises the following steps:
  a) reaction of a compound of general formula II:

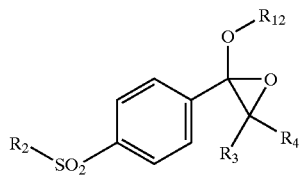

(II)

in which R$_2$, R$_3$ and R$_4$ are as defined above and R$_{12}$ represents a C$_1$–C$_6$ alkyl group, with an acid of general formula III:

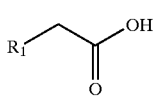

(III)

in which R$_1$ is as defined previously, in an anhydrous medium, in order to form a compound of formula IV:

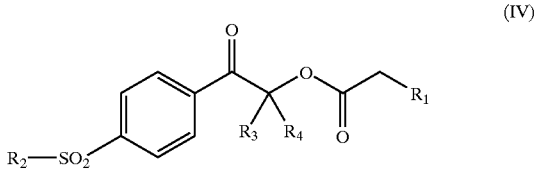

(IV)

R$_1$, R$_2$, R$_3$ and R$_4$ being as defined above;

b) reaction of the compound of formula IV with a strong base in an aprotic solvent in order to obtain an intermediate ring compound of formula V:

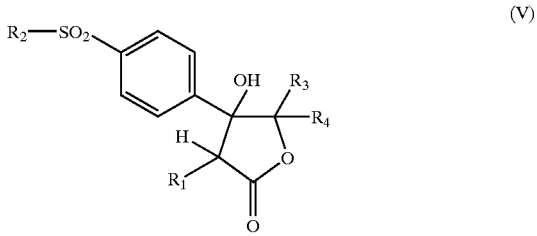

(V)

which, after elimination of a water molecule, forms a compound of general formula I; and c) isolation of the compound of general formula I thus obtained.

* * * * *

UNITED STATES PATENT AND TRADEMARK OFFICE
CERTIFICATE OF CORRECTION

PATENT NO. : 6,541,646 B2
DATED : April 1, 2003
INVENTOR(S) : Laetitia Canali et al.

It is certified that error appears in the above-identified patent and that said Letters Patent is hereby corrected as shown below:

<u>Title page,</u>
Item [75], Inventors, change "Lyons" to -- Lyon --.
Item [73], Assignee, change "Lyons" to -- Lyon --.

Signed and Sealed this

Twelfth Day of August, 2003

JAMES E. ROGAN
*Director of the United States Patent and Trademark Office*